United States Patent
Thambar et al.

(10) Patent No.: US 11,213,390 B2
(45) Date of Patent: *__Jan. 4, 2022__

(54) METHOD OF IMPLANTING A HEART VALVE PROSTHESIS

(71) Applicant: Percutaneous Cardiovascular Solutions Pty Ltd, North Albury (AU)

(72) Inventors: Suku Thambar, New South Wales (AU); Stayajit Rohan Jayasinghe, Southport (AU)

(73) Assignee: Percutaneous Cardiovascular Solutions Pty Ltd, North Albury (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/234,646

(22) Filed: Apr. 19, 2021

(65) Prior Publication Data

US 2021/0236283 A1    Aug. 5, 2021

Related U.S. Application Data

(60) Continuation of application No. 16/265,201, filed on Feb. 1, 2019, now Pat. No. 10,993,806, which is a
(Continued)

(51) Int. Cl.
*A61F 2/24* (2006.01)
*A61F 2/848* (2013.01)

(52) U.S. Cl.
CPC .............. *A61F 2/2427* (2013.01); *A61F 2/24* (2013.01); *A61F 2/2409* (2013.01);
(Continued)

(58) Field of Classification Search
CPC ........ A61F 2/24; A61F 2/2409; A61F 2/2412; A61F 2/2418
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |

(Continued)

FOREIGN PATENT DOCUMENTS

| | | |
|---|---|---|
| CA | 2304325 A1 | 10/2000 |
| CN | 101180010 A | 5/2008 |

(Continued)

OTHER PUBLICATIONS

Boudjemline, Younes, et al., "Steps Toward the Percutaneous Replacement of Atrioventricular Valves," JACC, vol. 46, No. 2, Jul. 19, 2005:360-5.
(Continued)

*Primary Examiner* — Javier G Blanco
(74) *Attorney, Agent, or Firm* — Klarquist Sparkman, LLP

(57) ABSTRACT

A method of implanting a percutaneous heart valve prosthesis via a catheter. The heart valve includes a valve body frame made of a nickel-titanium alloy. The valve body frame is collapsible for fitting within the catheter. A flexible skirt is sutured to the valve body frame for blocking blood flow between the valve body frame and native tissue. A one-way valve is positioned within the valve body frame for permitting blood to flow from a first end of the valve body frame to a second end. The one-way valve is preferably formed by three flexible valve leaflets made from a pericardial material. A plurality of barbs are spaced about the periphery of the valve body frame. Each of the barbs points toward the first end of the valve body frame and at least some of the barbs are positioned at the second end of the valve body frame.

8 Claims, 10 Drawing Sheets

Related U.S. Application Data continuation of application No. 14/623,301, filed on Feb. 16, 2015, now Pat. No. 10,213,298, which is a division of application No. 10/598,716, filed as application No. PCT/AU2005/000346 on Mar. 11, 2005, now Pat. No. 8,979,922.

(60) Provisional application No. 60/551,976, filed on Mar. 11, 2004.

(52) U.S. Cl.
CPC .......... *A61F 2/2412* (2013.01); *A61F 2/2418* (2013.01); *A61F 2/2436* (2013.01); *A61F 2/2487* (2013.01); *A61F 2002/8486* (2013.01); *A61F 2220/0016* (2013.01); *A61F 2220/0058* (2013.01); *A61F 2220/0075* (2013.01); *A61F 2230/005* (2013.01); *A61F 2230/0054* (2013.01); *A61F 2230/0067* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,218,783 A | 8/1980 | Reul et al. |
| 4,222,126 A | 9/1980 | Boretos et al. |
| 4,225,980 A | 10/1980 | Ramos Martinez |
| 4,274,437 A | 6/1981 | Watts |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,666,442 A | 5/1987 | Arru et al. |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,078,739 A | 1/1992 | Martin |
| 5,197,978 A | 3/1993 | Hess |
| 5,197,980 A | 3/1993 | Gorshkov et al. |
| 5,207,707 A | 5/1993 | Gourley |
| 5,326,371 A | 7/1994 | Love et al. |
| 5,332,402 A | 7/1994 | Teitelbaum |
| 5,370,685 A | 12/1994 | Stevens |
| 5,397,347 A | 3/1995 | Cuilleron et al. |
| 5,397,355 A | 3/1995 | Marin et al. |
| 5,405,381 A | 4/1995 | Olin |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,554,185 A | 9/1996 | Block et al. |
| 5,554,186 A | 9/1996 | Guo et al. |
| 5,575,818 A | 11/1996 | Pinchuk |
| 5,607,444 A | 3/1997 | Lam |
| 5,628,792 A | 5/1997 | Lentell |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,824,062 A | 10/1998 | Patke et al. |
| 5,855,601 A | 1/1999 | Bessler et al. |
| 5,861,029 A | 1/1999 | Evdokimov et al. |
| 5,861,030 A | 1/1999 | Rhee et al. |
| 5,868,782 A | 2/1999 | Frantzen |
| 5,879,381 A | 3/1999 | Moriuchi et al. |
| 5,902,334 A | 5/1999 | Dwyer et al. |
| 5,908,451 A | 6/1999 | Yeo |
| 5,908,452 A | 6/1999 | Bokros et al. |
| 5,935,108 A | 8/1999 | Katoh et al. |
| 5,954,766 A | 9/1999 | Zadno-Azizi et al. |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,051,022 A | 4/2000 | Cai et al. |
| 6,053,940 A | 4/2000 | Wijay |
| 6,086,612 A | 7/2000 | Jansen |
| 6,096,075 A | 8/2000 | Bokros et al. |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,616 B1 | 1/2001 | Brown, III |
| 6,210,432 B1 | 4/2001 | Solem et al. |
| 6,251,093 B1 | 6/2001 | Valley et al. |
| 6,280,466 B1 | 8/2001 | Kugler et al. |
| 6,296,663 B1 | 10/2001 | Patke et al. |
| 6,306,141 B1 | 10/2001 | Jervis |
| 6,312,465 B1 | 11/2001 | Griffin et al. |
| 6,332,893 B1 | 12/2001 | Mortier et al. |
| 6,336,938 B1 | 1/2002 | Kavteladze et al. |
| 6,352,543 B1 | 3/2002 | Cole |
| 6,358,277 B1 | 3/2002 | Duran |
| 6,440,164 B1 | 8/2002 | DiMatteo et al. |
| 6,445,630 B2 | 9/2002 | Ayadi et al. |
| 6,454,799 B1 | 9/2002 | Schreck |
| 6,458,153 B1 | 10/2002 | Bailey et al. |
| 6,475,237 B2 | 11/2002 | Drasler et al. |
| 6,482,228 B1 | 11/2002 | Norred |
| 6,485,489 B2 | 11/2002 | Teirstein et al. |
| 6,511,491 B2 | 1/2003 | Grudem et al. |
| 6,527,800 B1 | 3/2003 | McGuckin, Jr. et al. |
| 6,537,314 B2 | 3/2003 | Langberg et al. |
| 6,569,196 B1 | 5/2003 | Vesely |
| 6,569,198 B1 | 5/2003 | Wilson et al. |
| 6,602,281 B1 | 8/2003 | Klein |
| 6,610,088 B1 | 8/2003 | Gabbay |
| 6,616,684 B1 | 9/2003 | Vidlund et al. |
| 6,623,518 B2 | 9/2003 | Thompson et al. |
| 6,629,534 B1 | 10/2003 | St. Goar et al. |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | McGuckin, Jr. et al. |
| 6,712,836 B1 | 3/2004 | Berg et al. |
| 6,719,790 B2 | 4/2004 | Brendzel et al. |
| 6,723,038 B1 | 4/2004 | Schroeder et al. |
| 6,723,123 B1 | 4/2004 | Kazatchkov et al. |
| 6,730,118 B2 | 5/2004 | Spenser et al. |
| 6,733,525 B2 | 5/2004 | Yang et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 7,018,401 B1 | 3/2006 | Hyodoh et al. |
| 7,018,406 B2 | 3/2006 | Seguin et al. |
| 7,044,962 B2 | 5/2006 | Elliott |
| 7,087,088 B2 | 8/2006 | Berg et al. |
| 7,147,660 B2 | 12/2006 | Chobotov et al. |

(56) References Cited

U.S. PATENT DOCUMENTS

| | | |
|---|---|---|
| 7,147,661 B2 | 12/2006 | Chobotov et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,252,682 B2 | 8/2007 | Seguin |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,445,630 B2 | 11/2008 | Lashinski et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,556,645 B2 | 7/2009 | Lashinski et al. |
| 7,569,071 B2 | 8/2009 | Haverkost et al. |
| 7,585,321 B2 | 9/2009 | Cribier |
| 7,608,114 B2 | 10/2009 | Levine et al. |
| 7,621,948 B2 | 11/2009 | Herrmann et al. |
| 7,682,390 B2 | 3/2010 | Seguin |
| 7,748,389 B2 | 7/2010 | Salahieh et al. |
| 7,771,463 B2 | 8/2010 | Ton et al. |
| 7,785,360 B2 | 8/2010 | Freitag |
| 7,803,185 B2 | 9/2010 | Gabbay |
| 7,815,589 B2 | 10/2010 | Meade et al. |
| 7,824,443 B2 | 11/2010 | Salahieh et al. |
| 7,846,203 B2 | 12/2010 | Cribier |
| 7,892,281 B2 | 2/2011 | Seguin et al. |
| 7,914,569 B2 | 3/2011 | Nguyen et al. |
| 8,016,877 B2 | 9/2011 | Seguin et al. |
| 8,080,054 B2 | 12/2011 | Rowe |
| 8,109,996 B2 | 2/2012 | Stacchino et al. |
| 8,177,799 B2 | 5/2012 | Orban, III |
| 8,182,528 B2 | 5/2012 | Salahieh et al. |
| 8,182,530 B2 | 5/2012 | Huber |
| 8,197,528 B2 | 6/2012 | Colgan et al. |
| 8,216,301 B2 | 7/2012 | Bonhoeffer et al. |
| 8,221,482 B2 | 7/2012 | Cottone et al. |
| 8,246,675 B2 | 8/2012 | Zegdi |
| 8,246,678 B2 | 8/2012 | Salahieh et al. |
| 8,252,052 B2 | 8/2012 | Salahieh et al. |
| 8,303,653 B2 | 11/2012 | Bonhoeffer et al. |
| 8,317,854 B1 | 11/2012 | Ryan et al. |
| 8,361,137 B2 | 1/2013 | Perouse |
| 8,500,798 B2 | 8/2013 | Rowe et al. |
| 8,585,749 B2 | 11/2013 | Shelso |
| 8,617,236 B2 | 12/2013 | Paul et al. |
| 8,679,174 B2 | 3/2014 | Ottma et al. |
| 8,707,957 B2 | 4/2014 | Callister et al. |
| 8,721,708 B2 | 5/2014 | Seguin et al. |
| 8,740,974 B2 | 6/2014 | Lambrecht et al. |
| 8,828,078 B2 | 9/2014 | Salahieh et al. |
| 8,961,583 B2 | 2/2015 | Hojeibane et al. |
| 8,998,979 B2 | 4/2015 | Seguin et al. |
| 9,005,273 B2 | 4/2015 | Salahieh et al. |
| 9,011,521 B2 | 4/2015 | Haug et al. |
| 9,028,545 B2 | 5/2015 | Taylor |
| 9,241,792 B2 | 1/2016 | Benichou et al. |
| 2001/0007956 A1 | 7/2001 | Letac et al. |
| 2001/0018611 A1 | 8/2001 | Solem et al. |
| 2001/0047200 A1 | 11/2001 | White et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0111619 A1 | 8/2002 | Keast et al. |
| 2002/0198595 A1 | 12/2002 | Brendzel et al. |
| 2003/0014104 A1 | 1/2003 | Cribier |
| 2003/0023300 A1 | 1/2003 | Bailey et al. |
| 2003/0036791 A1 | 2/2003 | Philipp et al. |
| 2003/0036795 A1 | 2/2003 | Andersen et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0019378 A1 | 1/2004 | Hlavka et al. |
| 2004/0039442 A1 | 2/2004 | St. Goar et al. |
| 2004/0093060 A1 | 5/2004 | Seguin et al. |
| 2004/0106976 A1 | 6/2004 | Bailey et al. |
| 2004/0117009 A1 | 6/2004 | Cali et al. |
| 2004/0133273 A1 | 7/2004 | Cox |
| 2004/0152947 A1 | 8/2004 | Schroeder et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0043790 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2006/0020247 A1 | 1/2006 | Kagan et al. |
| 2006/0020327 A1 | 1/2006 | Lashinski et al. |
| 2006/0020332 A1 | 1/2006 | Lashinski et al. |
| 2006/0020333 A1 | 1/2006 | Lashinski et al. |
| 2006/0025854 A1 | 2/2006 | Lashinski et al. |
| 2006/0025855 A1 | 2/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladilah et al. |
| 2006/0116625 A1 | 6/2006 | Renati et al. |
| 2006/0173537 A1 | 8/2006 | Yang et al. |
| 2006/0195183 A1 | 8/2006 | Navia et al. |
| 2006/0206202 A1 | 9/2006 | Bonhoeffer et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0219620 A1 | 9/2007 | Eells et al. |
| 2008/0097581 A1 | 4/2008 | Shanley |
| 2009/0088832 A1 | 4/2009 | Chew et al. |
| 2009/0248149 A1 | 10/2009 | Gabbay |
| 2010/0114299 A1 | 5/2010 | Ben Muvhar et al. |
| 2011/0029067 A1 | 2/2011 | McGuckin, Jr. et al. |
| 2012/0041550 A1 | 2/2012 | Salahieh et al. |
| 2013/0006294 A1 | 1/2013 | Kashkarov et al. |
| 2014/0296973 A1 | 10/2014 | Bergheim et al. |
| 2014/0309728 A1 | 10/2014 | Dehdashtian et al. |
| 2015/0012085 A1 | 1/2015 | Salahieh et al. |
| 2015/0018938 A1 | 1/2015 | Von Segesser et al. |

FOREIGN PATENT DOCUMENTS

| | | | |
|---|---|---|---|
| EP | 0170262 | A2 | 2/1986 |
| EP | 1057460 | A1 | 12/2000 |
| EP | 1255510 | A1 | 11/2002 |

(56) References Cited

FOREIGN PATENT DOCUMENTS

| | | | |
|---|---|---|---|
| EP | 1259194 B1 | 11/2002 |
| EP | 1264582 A2 | 12/2002 |
| EP | 1281375 A2 | 2/2003 |
| EP | 1356792 A1 | 10/2003 |
| EP | 1356793 A2 | 10/2003 |
| EP | 1472996 A1 | 11/2004 |
| EP | 1734903 A1 | 12/2006 |
| EP | 2308425 A1 | 4/2011 |
| EP | 2319458 A1 | 5/2011 |
| GB | 1264471 A | 2/1972 |
| GB | 1315844 A | 5/1973 |
| GB | 2245495 A | 1/1992 |
| GB | 2398245 A | 8/2004 |
| JP | 2002540889 A | 12/2002 |
| WO | 9117720 A1 | 11/1991 |
| WO | 9749355 A1 | 12/1997 |
| WO | 0047139 A1 | 8/2000 |
| WO | 0053104 A1 | 9/2000 |
| WO | 0061034 A1 | 10/2000 |
| WO | 0112105 A1 | 2/2001 |
| WO | 0135861 A1 | 5/2001 |
| WO | 0156512 A1 | 8/2001 |
| WO | 0172239 A2 | 10/2001 |
| WO | 0230335 A2 | 4/2002 |
| WO | 0236048 A1 | 5/2002 |
| WO | 02085251 A1 | 10/2002 |
| WO | 03003949 A2 | 1/2003 |
| WO | 03011195 A2 | 2/2003 |
| WO | 03028558 A2 | 4/2003 |
| WO | 03049648 A2 | 6/2003 |
| WO | 03088873 A1 | 10/2003 |
| WO | 03092554 A1 | 11/2003 |
| WO | 2004014258 A1 | 2/2004 |
| WO | 2004019811 A2 | 3/2004 |
| WO | 2004023980 A2 | 3/2004 |
| WO | 2004082527 A2 | 9/2004 |
| WO | 2004093728 A2 | 11/2004 |
| WO | 2005002466 A2 | 1/2005 |
| WO | 2005009285 A2 | 2/2005 |
| WO | 2005011534 A1 | 2/2005 |
| WO | 2005020842 A2 | 3/2005 |
| WO | 2005041810 A2 | 5/2005 |
| WO | 2005062980 A2 | 7/2005 |
| WO | 2005087140 A1 | 9/2005 |
| WO | 2006054107 A2 | 5/2006 |
| WO | 2006085304 A2 | 8/2006 |
| WO | 2006089236 A1 | 8/2006 |
| WO | 2006111391 A1 | 10/2006 |
| WO | 2006127756 A2 | 11/2006 |
| WO | 2007025028 A1 | 3/2007 |
| WO | 2007034488 A2 | 3/2007 |
| WO | 2007058857 A2 | 5/2007 |
| WO | 2007100410 A2 | 9/2007 |
| WO | 2007130537 A1 | 11/2007 |
| WO | 2007149933 A2 | 12/2007 |
| WO | 2008100599 A1 | 8/2008 |
| WO | 2008100600 A1 | 8/2008 |
| WO | 2009045331 A1 | 4/2009 |
| WO | 2009052180 A1 | 4/2009 |
| WO | 2009052188 A1 | 4/2009 |

OTHER PUBLICATIONS

Clement et al., "Continual Coordination through Shared Activities," Proceedings of the Second International Joint Conference on Autonomous Agents and Multiagent Systems, Dec. 31, 2003, pp. 57-64.

Jeffrey S. Borer et al. Contemporary Approach to Aortic and Mitral Regurgitation, Circulation 2003, 106:2432.

Khambadkone et al., "Percutaneous implantation of atrioventricular valves: concept and early animal experience," EuroIntervention, vol. 1 Supplement A, May 20, 2006, A24-A25.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Ma, Liang, et al., "Double-Crowned Valved Stents For Off-Pump Mitral Valve Replacement," European Journal of Cardio-thoracic Surgery 28 (2005) 194-199, Applicant believes this may have been available as early as August of 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

METHOD OF IMPLANTING A HEART VALVE PROSTHESIS

CROSS REFERENCE TO RELATED APPLICATIONS

This application is a continuation of U.S. application Ser. No. 16/265,201, filed Feb. 1, 2019, now U.S. Pat. No. 10,993,806, which is a continuation of U.S. application Ser. No. 14/623,301, filed Feb. 16, 2015, now U.S. Pat. No. 10,213,298, which is a divisional of U.S. application Ser. No. 10/598,716, filed May 28, 2008, now U.S. Pat. No. 8,979,922, which is the National Stage of International Application No. PCT/AU2005/000346, filed Mar. 11, 2005, which claims the benefit of U.S. Provisional Application No. 60/551,976, filed Mar. 11, 2004, the entire disclosures of which are incorporated by reference in their entireties.

FIELD OF THE INVENTION

The present invention relates to a percutaneous heart valve prosthesis, and particularly relates to, but is not limited to, a percutaneous mitral valve prosthesis.

BACKGROUND OF THE INVENTION

Heart valve regurgitation is a condition whereby the heart valve does not seal completely as a result of disease or injury, and may have fatal consequences.

Malfunctioning heart valves have typically been replaced with mechanical or biologic heart valve prostheses using highly invasive open-heart surgery techniques. Whilst there has been some success in developing replacement aortic valve prostheses for delivery via percutaneous catheter-based methods, these techniques have not been particularly successful when applied to mitral valve prostheses.

Mitral valve replacement is firstly made difficult as a result of the anatomy of the mitral valve, and particularly that of the mitral valve annulus in which the mitral valve is leaflets are located. The mitral valve annulus is typically very distorted, and of unpredictable and non-uniform geometries, as compared to the relatively uniform aortic valve annulus. This unpredictable anatomy makes it difficult to design a pre-constructed mitral valve prosthesis that would fit the mitral valve annulus in a satisfactory manner for safe, stable and meticulous deployment.

Further, unlike the aortic valve annulus which is entirely surrounded by muscular tissue, the mitral valve annulus is bounded by muscular tissue on the outer wall only, with the inner side of the mitral valve annulus being bounded by a thin vessel wall which separates the mitral valve annulus and the aortic outflow tract. As a result, the mitral valve annulus cannot be subjected to any significant radial forces, as would be typical with an expanding stent type of valve prosthesis, as such radial forces would tend to collapse the aortic outflow tract, resulting in circulatory collapse with likely fatal consequences. As a result of these difficulties, firm anchoring of a deployed mitral valve prosthesis is currently not readily obtainable.

Mitral valve replacement techniques have also generally advocated removal of the native valve prior to location of the replacement mitral valve prosthesis. This is a technically extremely challenging task associated with the potentially fatal complication of profound mitral regurgitation that may not be adequately addressed by the subsequent valve replacement. The lack of an effective mitral valve may lead to overwhelming hemodynamic instability that may not be tolerated by the already compromised left ventricle and overwhelming pulmonary edema may rapidly result.

OBJECT OF THE INVENTION

It is the object of the present invention to overcome or substantially ameliorate at least one of the above disadvantages.

SUMMARY OF THE INVENTION

There is disclosed herein a percutaneous heart valve prosthesis comprising:

a valve body having a valve body first end, a valve body second end and a passage extending along a longitudinal axis between said valve body first end and said valve body second end, said valve body being collapsible about said longitudinal axis for delivery via catheter;

one or more flexible valve elements secured to said valve body and extending across said passage for blocking blood-flow in one direction through said passage;

an anchor device, said anchor device being collapsible for delivery via catheter; and an anchor line secured to and extending between said valve body and said anchor device.

The anchor device may comprise a collapsible anchor frame formed of elongate elastic anchor frame elements. The anchor frame may be collapsible from a stable substantially flat plate-like configuration to an unstable elongate configuration for location within a catheter. The anchor frame elements may each be formed of a superelastic shape memory material.

The valve body may comprise a collapsible valve body frame formed of elongate elastic valve body elements. The valve body frame elements may each be formed of a superelastic shape memory material.

The valve body typically tapers toward said valve body first end. The anchor line is then usually secured to said valve body first end.

The valve body frame may comprise at least three valve body sub-frame members, each said valve body sub-frame member having the general form of a deltoid, each said deltoid having acute-angled vertices at said valve body first and second ends, and oblique-angled vertices located between said valve body first and second ends. Each valve body sub-frame member may have the general form of a rhombus.

The valve body sub-frame members may be joined at respective said oblique-angled vertices.

Each sub-frame member may further comprise a collapsible diagonal element extending between said oblique-angled vertices. The one or more valve elements is/are generally secured to the diagonal elements.

The valve body frame may alternatively be in the general form of a collapsible cylindrical ring.

The prosthesis may further comprise a plurality of prongs spaced about a periphery of said valve body for engaging the native wall of a valve orifice in use.

The prosthesis may still further comprise a flexible skirt extending about a periphery of said valve body for blocking blood flow in said one direction between said valve body and the native wall of a valve orifice in use. Said flexible skirt may be formed of biological material, typically pericardial material.

The prosthesis is typically a mitral valve prosthesis.

There is further disclosed herein a percutaneous heart valve replacement system comprising:

a catheter having a catheter first end and a catheter second end;

a prosthesis as defined above located in said catheter, said valve body being in a collapsed state and located towards said catheter first end, said anchor device being in a collapsed state and located between said valve body and said catheter second end; and an elongate guide element having a guide element first end and a guide element second end, said guide element first end being detachably attached to said anchor device and said guide element second end extending beyond said catheter second end.

There is further disclosed herein a method of treating a failed or failing mitral valve comprising the steps of:

advancing a first end of a catheter through the venous system of a patient to be treated into the right atrium of the patient's heart;

creating a puncture in the inter-atrial septum of the heart;

advancing said catheter first end through said puncture, into the left atrium, through the native mitral valve and into the left ventricle of the heart;

locating a prosthesis as defined above in said catheter with said valve body and said anchor device in a collapsed state, said valve body being located between said anchor device and said catheter first end;

advancing said prosthesis through said catheter until said valve body is released from said catheter first end, thereby expanding said valve body from said collapsed state;

withdrawing said catheter first end through the mitral valve into the left atrium;

withdrawing said valve body toward the left atrium, locating said valve body in the orifice of the native mitral valve;

withdrawing said catheter first end through said puncture and into said right atrium;

advancing said anchor device through said catheter until said anchor device is released from said catheter first end, thereby expanding said anchor device from said collapsed state;

engaging said anchor device with said inter-atrial septum about said puncture; and withdrawing said catheter from the patient.

There is yet further disclosed herein a percutaneous heart valve prosthesis comprising:

a valve body having a valve body first end, a valve body second end and a passage extending along a longitudinal axis between said valve body first end and said valve body second end, said valve being collapsible about said longitudinal axis for delivery via catheter;

one or more flexible valve elements secured to said valve body and extending across said passage for blocking bloodflow in one direction through said passage;

wherein said valve body tapers toward said valve body first end, said valve body first end being sized to pass through a valve orifice associated with a heart valve to be replaced, said valve body second end being sized so as not to pass through the valve orifice.

The valve body may comprise a collapsible valve body frame formed of elongate elastic valve body elements. The valve body frame elements may each be formed of a superelastic shape memory material.

The valve body frame may comprise at least three valve body sub-frame members, each said valve body sub-frame member having the general form of a deltoid, each said deltoid having acute-angled vertices at said valve body first and second ends, and oblique-angled vertices located between said valve body first and second ends. Each valve body sub-frame member may have the general form of a rhombus.

The valve body sub-frame members may be joined at respective said oblique-angled vertices.

Each sub-frame member may further comprise a collapsible diagonal element extending between said oblique-angled vertices. The one or more valve elements is/are generally secured to said diagonal elements.

The prosthesis is typically a mitral valve prosthesis.

There is yet further disclosed herein a percutaneous heart valve replacement system comprising:

a catheter having a catheter first end and a catheter second end;

a prosthesis as defined above located in said catheter, said valve body being in a collapsed state and located towards said catheter first end; and an elongate guide element having a guide element first end and a guide element second end, said guide element first end being detachably attached to said prosthesis and said guide element second end extending beyond said catheter second end.

There is further disclosed herein a method of treating a failed or failing heart valve comprising the steps of:

advancing a first end of a catheter through the venous system of a patient to be treated into the right atrium of the patient's heart;

creating a puncture in the inter-atrial septum of the heart;

advancing said catheter first end through said puncture, into the left atrium, through the native mitral valve and into the left ventricle of the heart;

locating a prosthesis as defined above in said catheter with said valve body in a collapsed state and said valve body second end located between said valve body first end and said catheter first end;

advancing said prosthesis through said catheter until said valve body is released from said catheter first end, thereby expanding said valve body from said collapsed state;

withdrawing said catheter first end through the mitral valve into the left atrium;

withdrawing said valve body toward the left atrium, wedging said valve body in the orifice of the native mitral valve; and withdrawing said catheter from the patient.

There is still further disclosed herein a percutaneous heart valve prosthesis comprising:

a valve body having a valve body first end, a valve body second end and a passage extending along a longitudinal axis between said valve body first end and said valve body second end, said valve body being collapsible about said longitudinal axis for delivery via catheter;

one or more flexible valve elements secured to said valve body and extending across said passage for blocking bloodflow in one direction through said passage;

a flexible skirt extending about a periphery of said valve body for blocking bloodflow in said one direction between said valve body and the native wall of a valve orifice in use.

The flexible skirt may be formed of biological material, typically pericardial material.

The prosthesis is typically a mitral valve prosthesis.

There is still further disclosed herein a percutaneous heart valve replacement system comprising:

a catheter having a catheter first end and a catheter second end;

a prosthesis as defined above located in said catheter, said valve body being in a collapsed state and located towards said catheter first end; and an elongate guide element having a guide element first end and a guide element second end, said guide element first end being detachably attached to said prosthesis and said guide element second end extending beyond said catheter second end.

There is further disclosed herein a method of treating a failed or failing mitral valve comprising the steps of:

advancing a first end of a catheter through the venous system of a patient to be treated into the right atrium of the patient's heart;

creating a puncture in the inter-atrial septum of the heart;

advancing said catheter first end through said puncture, into the left atrium, through the native mitral valve and into the left ventricle of the heart;

locating a prosthesis as defined above in said catheter with said valve body in a collapsed state;

advancing said prosthesis through said catheter until said valve body is released from said catheter first end, thereby expanding said valve body from said collapsed state;

withdrawing said catheter first end through the mitral valve into the left atrium;

withdrawing said valve body toward the left atrium, locating said valve body in the orifice of the native mitral valve with said skirt located toward the left ventricle; and withdrawing said catheter from the patient.

BRIEF DESCRIPTION OF THE DRAWINGS

Preferred forms of the present invention will now be described by way of example with reference to the accompanying drawings, wherein.

DETAILED DESCRIPTION OF THE PREFERRED EMBODIMENTS

Figure 1:
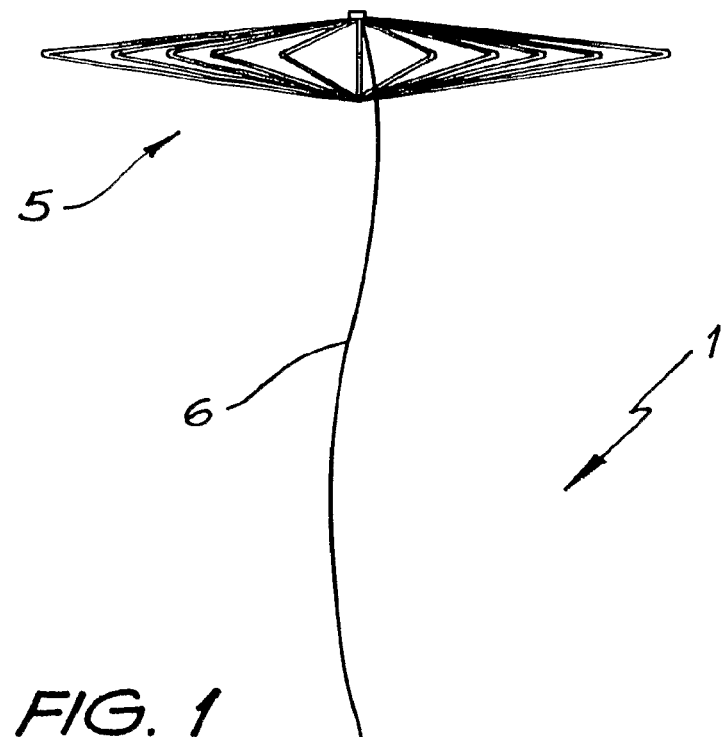
FIG. 1 is a front elevation view of a percutaneous mitral valve prosthesis.
Figure 1:
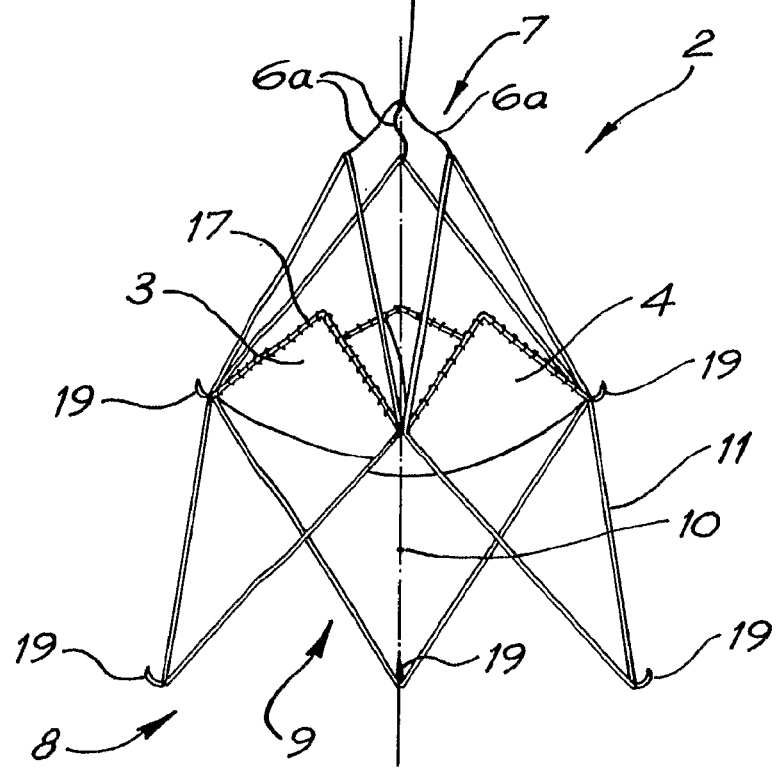

Referring specifically to FIG. 1, a percutaneous heart valve prosthesis, in the form of a mitral valve prosthesis 1, comprises a valve body 2, first and second flexible valve elements 3, 4, an anchor device 5 and an anchor line 6 secured to and extending between the valve body 2 and the anchor device 5.

The valve body 2 has a first end 7 and a second end 8. A blood flow passage 9 extends along a longitudinal axis 10 between the valve body first end 7 and the valve body second end 8. The valve body 2 is configured so as to be collapsible about the longitudinal axis 10 to enable the valve body 2 to be located in a catheter for delivery of the prosthesis 1, as will be discussed further below.

The valve 2 is in the form of a collapsible valve body frame formed of elongate elastic valve body frame elements 11. Each of the valve body frame elements 11 may be suitably formed as wires of a superelastic shape memory material. A particularly suitable material is nitinol, a nickel-titanium alloy, which is known for use in percutaneous prosthesis applications. Other suitable elastic metallic materials include stainless steel, gold, other titanium alloys and cobalt chromium molybdenum. Other suitably rigid yet elastic metal alloys, or non-metallic materials, may also be utilized as desired. The valve body frame elements 11 will typically have a thickness of the order of 0.3 to 0.4 mm, however elements of varying diameter are also envisaged.

Figure 2:
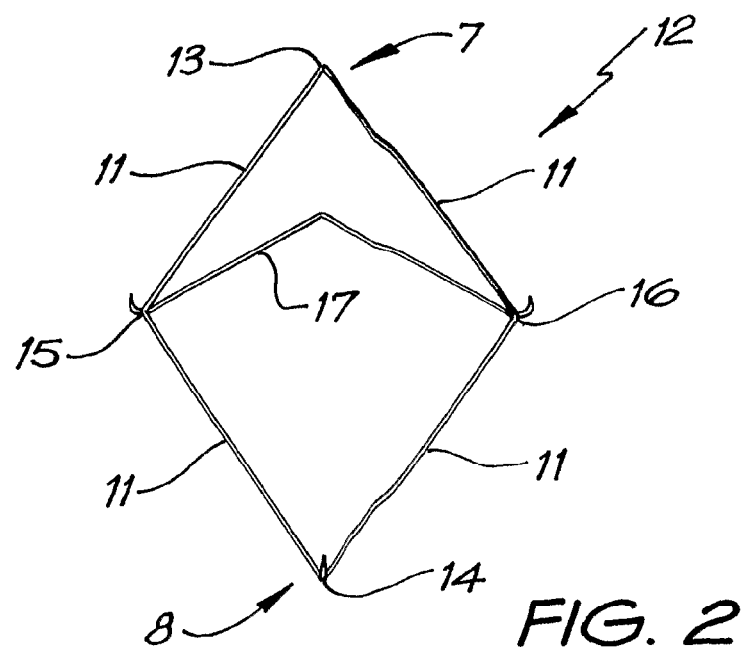
FIG. 2 is a front elevation view of a sub-frame member of the valve body of the prosthesis of FIG. 1.

The valve body frame 2 depicted in FIG. 1 comprises three valve body sub-frame members 12. One such valve body sub-frame member 12 is depicted in FIG. 2. As can best be seen from FIG. 2, each valve body sub-frame member 12 is in the general form of a deltoid, and here particularly in the form of a diamond or rhombus (that is, a deltoid with four equal length sides). Each valve body sub-frame member 12 is arranged such that the acute-angled vertices 13, 14 of the rhombus are arranged at the valve body first and second ends 7, 8, with the oblique-angled vertices 15, 16 located between the valve body first and second ends 7, 8.

Each valve body sub-frame member 12 will generally be formed of two wires, kinked to form the oblique-angled vertices 15, 16, with the ends of each wire being soldered to form the acute-angled vertices 13, 14, thereby providing the rhombus form.

Alternatively, the wires could be kinked to form the acute-angled vertices 13, 14, with the ends soldered at the oblique-angled vertices 15, 16.

Adjacent valve body sub-frame members 12 are joined at their respective oblique-angled vertices 15, 16 as depicted in FIG. 1, typically by soldering. Alternatively, the adjacent valve body sub-frame members may be sutured or joined by any other suitable means. Whilst, in the valve body 2 depicted, three sub-frame members 12 are joined so as to provide a generally triangular transverse cross-section, more than three sub-frame members may be utilized as desired such that the transverse cross-section of the valve body 2 becomes gradually more circular in shape with the addition of further body sub-frame members 12.

As is particularly apparent from FIG. 1, the valve body 2 is arranged such that it tapers towards the valve body first end 7. The valve body is tapered and sized such that the valve body first end 7 is able to pass through a mitral valve orifice associated with a mitral valve to be replaced, with the valve body second end 8 being sized so as not to pass through such a mitral valve orifice, when in the uncollapsed state. A mitral valve orifice in an adult person typically has a diameter of the order of 25 mm.

Referring again particularly to FIG. 2, each valve body sub-frame member 12 may further comprise a collapsible diagonal element 17 extending between the oblique-angled vertices 15, 16. The diagonal elements will typically be in the form of a kinked wire formed of the same material as the remaining elements 11 of the valve body sub-frame member 12. The kink is provided in the diagonal element 17 to enable it to readily collapse to allow delivery via catheter.

Figure 3:
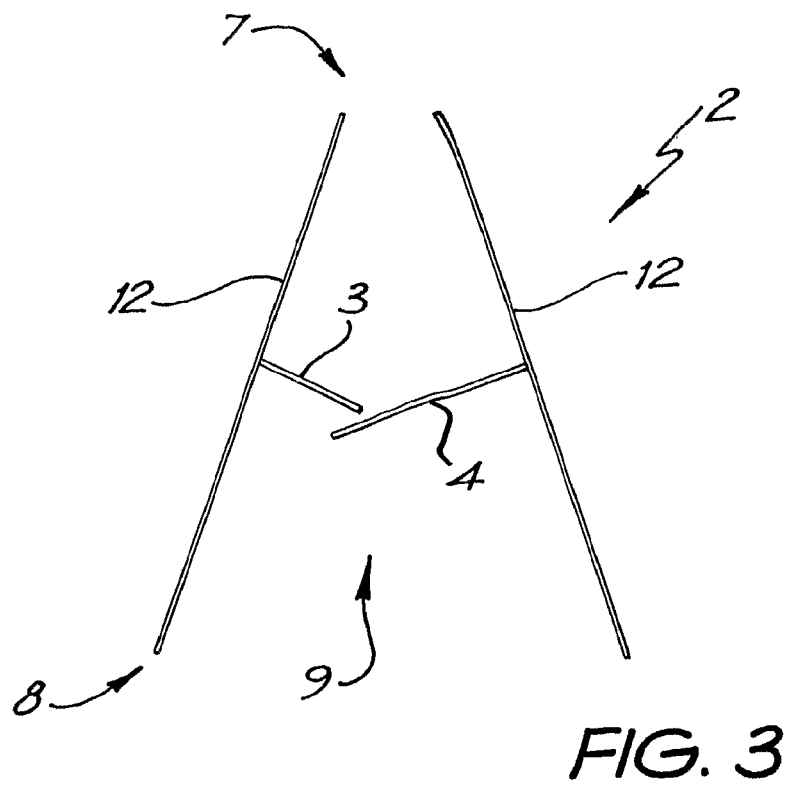
FIG. 3 is a schematic cross sectional front elevation view of the valve body of the prosthesis of FIG. 1.

Referring to FIGS. 1 and 3, the valve elements 3, 4, in the form of valve leaflets, are secured to the valve body 2 on opposing sides of the bloodflow passage 9. Typically, the valve leaflets 3, 4 will be sutured to the diagonal elements 17 of the valve body sub-frame members 12. The valve leaflets 3, 4 are here overlapping, typically with a shorter leaflet 3 overlapped by a longer leaflet 4 lying between the shorter leaflet 3 and the valve body second end 8, such that, in use, the longer leaflet 4 lies on the outer or ventricular side of the valve body 2. Referring to FIG. 3, it can be seen that sub-frame members 12 are planar.

The valve leaflets 3, 4 are configured in a known manner so as to open toward the valve body second end 8, allowing bloodflow through the passage 9 in a direction from the valve body first end 7 toward the valve body second end 8, and to sealingly lock in response to pressure acting in the opposite direction, so as to block bloodflow through the passage 9 in the reverse or retrograde direction. The valve leaflets may be formed of biological material, such as pericardial material, as is well known in the art, or of any other suitable flexible valve materials known in the art, including woven metallic materials or non-metallic materials such as silicone. The valve leaflets may be sutured to the diagonal element 17 around the entire periphery of the passage 9, or may be hinged only at one or more discrete points around the periphery of the passage 9. Any of various well known valve leaflet configurations may be utilized so as to provide the one way valve function required, including configurations utilizing one valve leaflet only or utilizing three or more valve leaflets as is known in the art. Alternatively, a single valve element in the general form of a windsock might be utilized.

Figure 4:
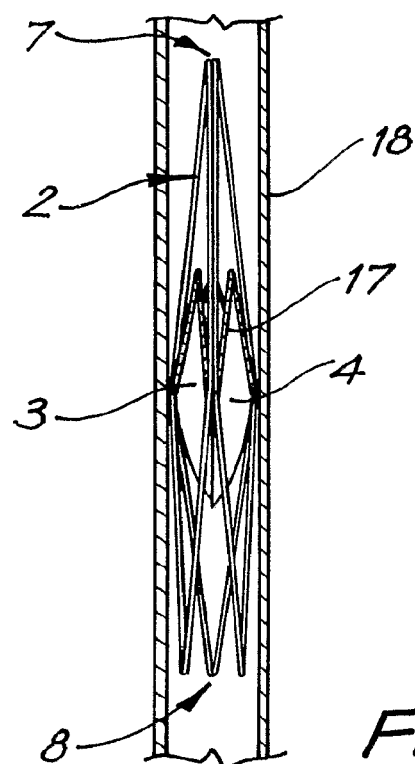
FIG. 4 is a front elevation view of the valve body of the prosthesis of FIG. 1 in a collapsed state located in a catheter.

Referring to FIG. 4, the configuration of the valve body 2 facilitates it being collapsed about the longitudinal axis 10, enabling it to fit within a catheter 18 for subsequent percutaneous deployment.

As depicted in FIGS. 1 and 2, prongs, typically in the form of barbs 19, may be spaced about the periphery of the valve body 2, typically at or adjacent the oblique-angled vertices 15, 16 of each sub-frame element, for engaging the native annular wall surrounding a valve orifice in use, as will be discussed below. Further barbs may be located at the acute-angled vertices 24 at the valve body second end 8. The barbs 19 will typically point toward the end 7, when the anchor line 6 is secured to the valve body first end 7.

Figure 5:
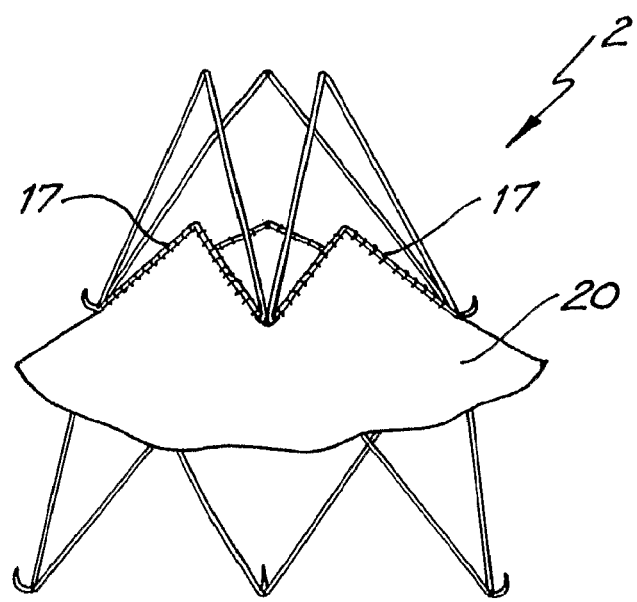
FIG. 5 is a front elevation view of an alternate valve body of a percutaneous mitral valve prosthesis.

Referring to FIG. 5, a flexible skirt 20 may extend around the periphery of the valve body 2 for blocking retrograde bloodflow toward the valve body first end 7, between the valve body 2 and the native wall surrounding the mitral orifice in use. The flexible skirt 20 will typically be sutured to the diagonal element 17 of each valve body sub-frame member 12, and as such will effectively provide a continuation of the valve leaflets 3, 4 on the exterior of the valve body 2. The flexible skirt 20 may be formed of biological material, such as pericardial material, or alternatively might be formed of any suitable flexible non-biologic material, such as, for example, silicone, polyester or dacron.

Figure 6:
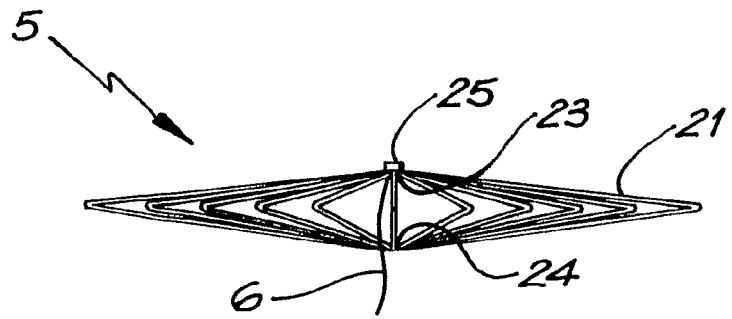
FIG. 6 is a front elevation view of the anchor device of the prosthesis of FIG. 1.

Referring to FIG. 6, the anchor device 5 will also typically comprise a collapsible anchor frame formed of elongate anchor frame elements 21. The anchor frame elements 21 will again typically be formed of a superelastic shape memory material as per the valve body elements 11, and may again be formed of nitinol or other suitable elastic materials. Here the anchor device frame 5 is formed of an array of anchor sub-frame members 22. Each anchor sub-frame member has the general form of a rhombus. Rather than being joined side to side as per the valve body sub-frame members 12, however, the anchor sub-frame members 22 are here each joined in a radial pattern at their oblique-angled vertices 23, 24.

Figure 7:
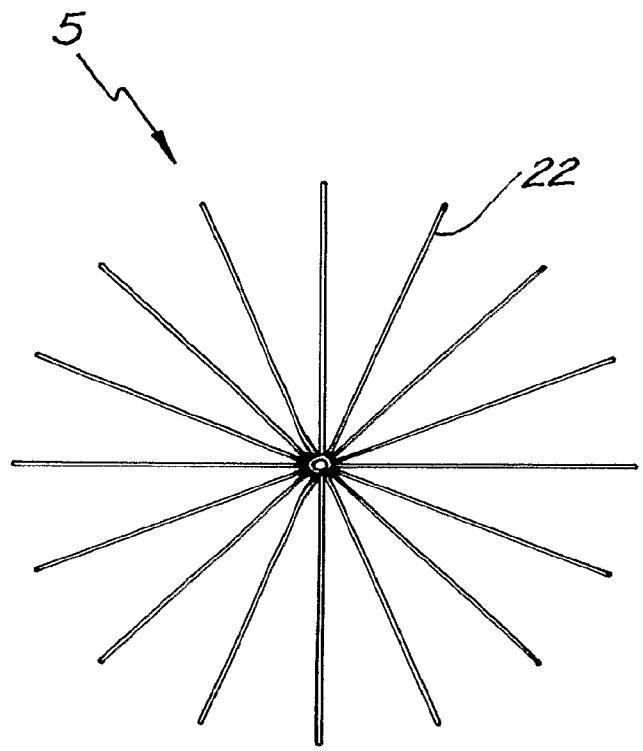
FIG. 7 is a plan view of the anchor device of FIG. 6.
Figure 8:
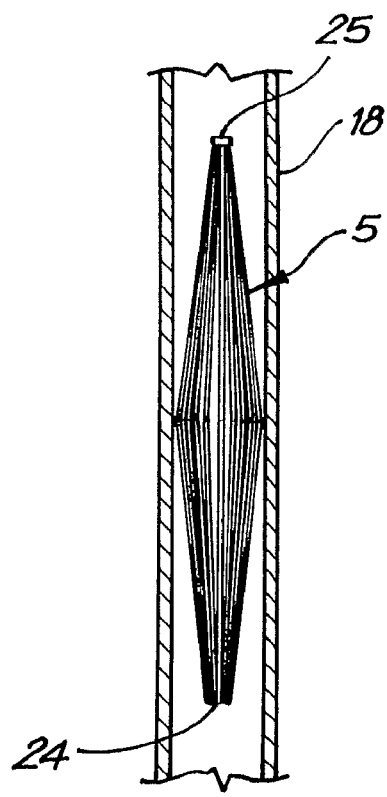
FIG. 8 is a front elevation view of the anchor device of FIG. 6 in a collapsed state located in a catheter.

Accordingly, the anchor device 5 is collapsible from a stable substantially flat plate-like configuration (as depicted in FIGS. 6 and 7) to an unstable elongate configuration for location within a catheter 18 (as particularly depicted in FIG. 8). The anchor device 5 is provided at one end, corresponding to the oblique-angled vertices 23, with a coupling 25 for releasably coupling to a guide element as will be discussed below. The coupling 25 may suitably be in the form of a threaded aperture.

The anchor line 6 will also generally be secured to the end of the anchor device 5 corresponding to the oblique-angled vertices 23, and will extend through the length of the anchor device 5 beyond the opposing oblique-angled vertices 24, such that tension applied to the anchor line 6 will tend to retain the anchor device 5 in the flat configuration. The anchor line 6 may be formed of any suitable flexible wire or cord, and may be suitably formed again of nitinol wire or stainless steel wire. Other suitable materials may include carbon fiber, polyimides or aromatic polyamides. Where elasticity in the anchor line is desired, other suitable materials may include polyether block amide (PEBAX), silicone or polyurethane.

The opposing end of the anchor line 6 will typically be secured to the valve body first end 7, typically by way of three further lines 6a converging from the acute angled-vertices 13 of each-frame member 12 of the valve body 2. Where desired, further anchor lines 6 extending between the valve body 2 and anchor device 5 may be utilized.

The structure of the valve body 1 and anchor device 5 may be covered with biological material or less thrombogenic material to reduce the possibility of blood clotting around the non-biological material from which the valve body 2 and anchor device 5 will typically be formed.

A surgical procedure for replacement of a native mitral valve 101 utilizing the prosthesis 1 will now be described with reference to FIGS. 9 to 15. Given that the native mitral valve 101 and mitral valve orifice 102 will generally vary in size between patients, measurements of the native mitral valve 101 and orifice 102 may be made with the use of a compliant balloon and transthoracic and transesophageal echocardiography.

The compliant balloon is located in the valve orifice 102 and expanded so as to move the leaflets of the native valve 101 out of the way and enable measurement of the diameter of the mitral valve orifice 102. A measurement of the distance between the native mitral valve 101 and the region of the inter-atrial septum 103 is also taken.

Based on the measurements taken, a suitably sized prosthesis valve body 2 is selected to fit the size of the mitral valve orifice 102 such that the valve leaflets 3, 4, will be positioned in the vicinity of the native valve 101. The measurement of the distance between the native mitral valve 101 and the mid region of the inter-atrial septum 103 is also utilized to determine the length of the anchor line 6 extending between the valve body 2 and anchor device 5, such that the anchor line 6 will be taught when the prosthesis 1 is deployed, as will be discussed further below.

The venous system of the patient to be treated is accessed via a puncture 104, typically in the groin area, accessing the femoral vein 105. Access to the venous system might alternatively be made via other large peripheral veins such as the subclavian or jugular veins. The femoral vein 105 is, however, preferred given the compressibility of the femoral vein 105 once a catheter is removed from the patient to achieve haemostasis.

Figure 9:
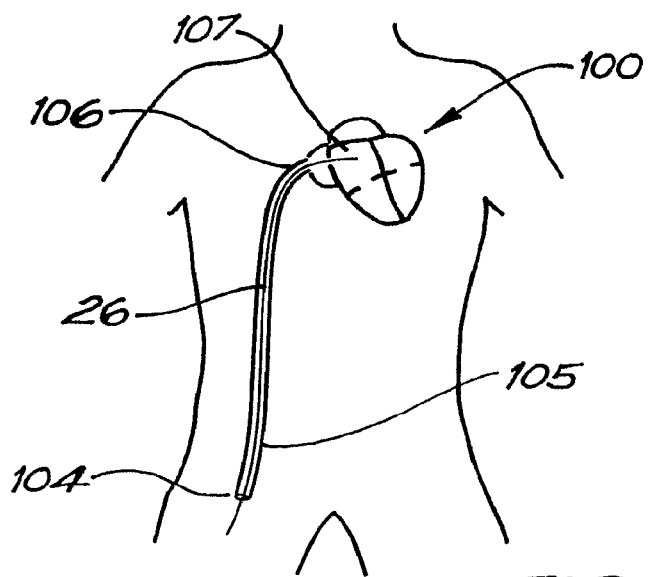
FIG. 9 is a schematic front elevation view of a patient depicting a guide wire accessing the patient's heart.

A guide wire 26, typically having a diameter of approximately 0.85 to 1.7 mm, is then inserted through the puncture 104 and along the femoral vein 105 and via the inferior vena cava 106 to the right atrium 107 of the patient's heart 100 as depicted in FIG. 9. If additional steadying of the guide wire 26 is desired, a snare may be introduced to the heart 100 through an arterial approach from the left or right femoral artery, aorta and aortic valve. The snare will then engage a J-tip on the end of the guide wire 26 and draw the end of the guide wire 26 through the arterial system to the exterior of the patient so that opposing ends of the guide wire 26 may be steadied.

Figure 10:
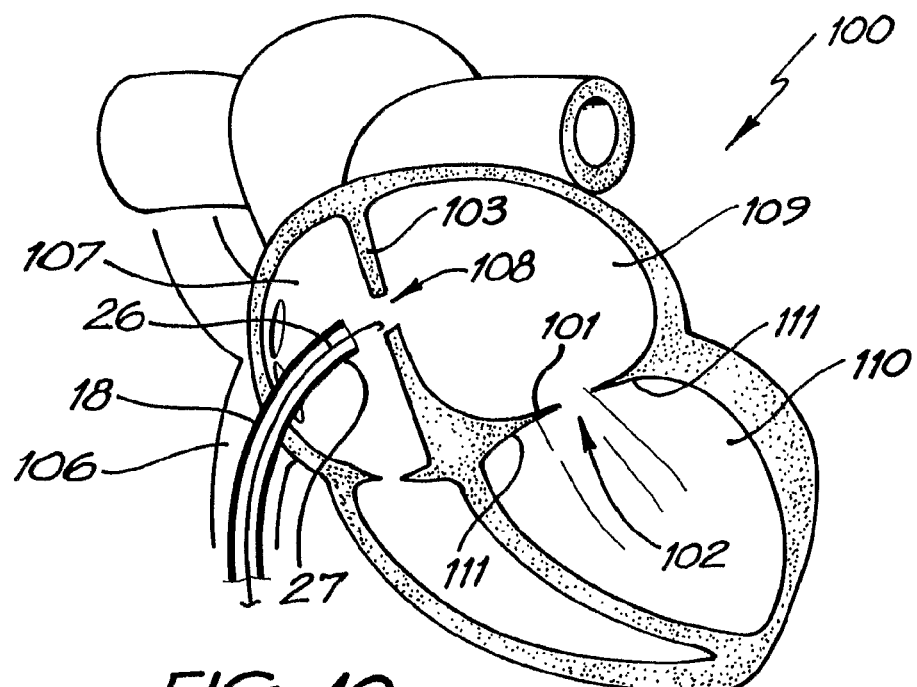
FIG. 10 is a schematic cross-sectional front elevation view of a heart depicting a catheter advanced into the right atrium and a puncture formed in the inter-atrial septum.
Figure 11:
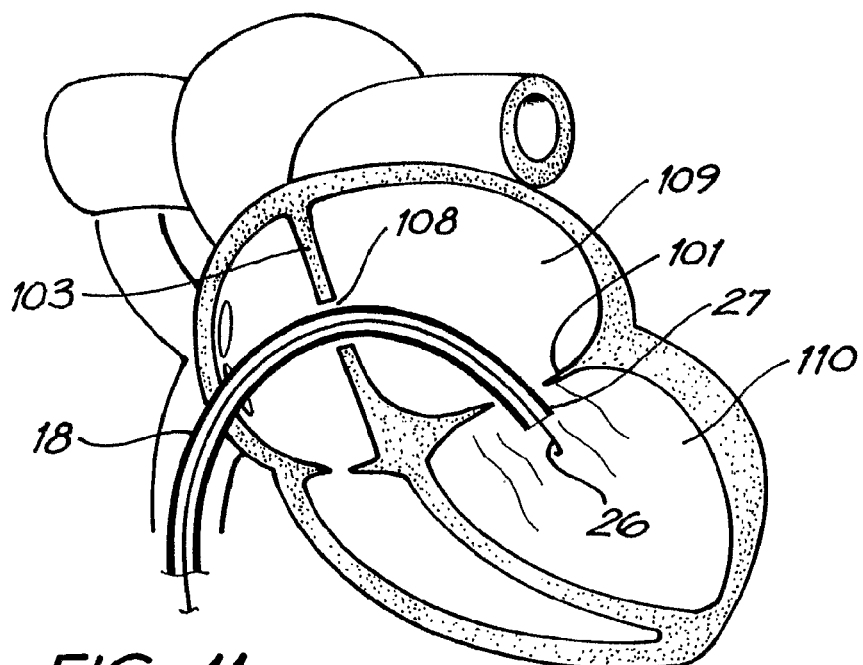
FIG. 11 is a cross-sectional front elevation view of the heart of FIG. 10 with the catheter advanced into the left ventricle.

A catheter 18, typically having an internal diameter of at least 8 French (approximately 2.8 mm) is then advanced over the guide wire 26 and into the right atrium 107. Referring to FIG. 10, a puncture 108 is then made in the inter-atrial septum 103 using conventional equipment advanced via the catheter 18 in the known manner. The guide wire 26 and catheter 18 are then further advanced through the septal puncture 108 into the left atrium 109, through the native mitral valve 101 and into the left ventricle 110 as shown in FIG. 11. The first end 27 of the catheter 18 is thus located in the left ventricle 110 whilst the opposing second end of the catheter 18 is still located on the exterior of the patient.

Figure 12:
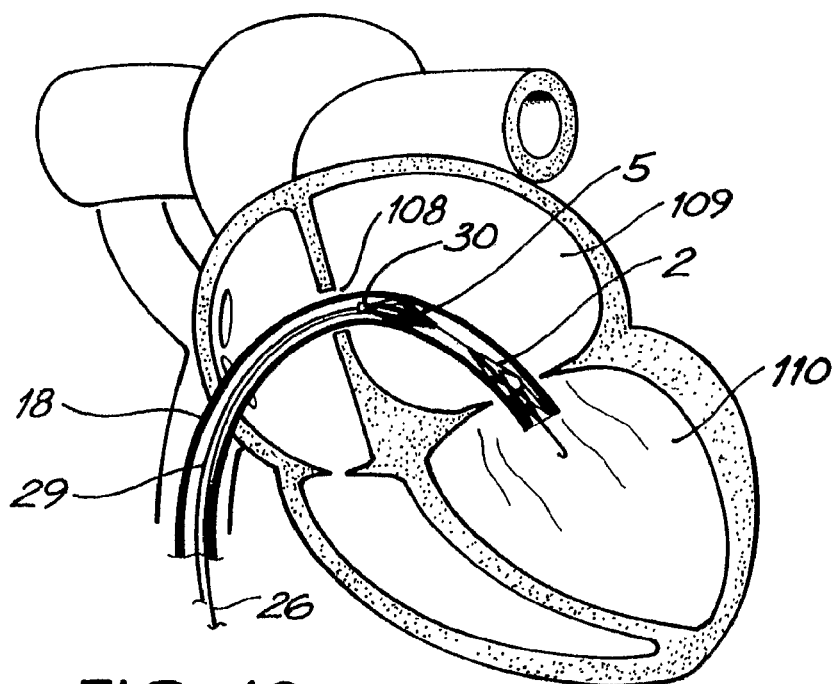
FIG. 12 is a schematic cross-sectional front elevation view of the heart of FIG. 10 with a percutaneous heart valve prosthesis advanced through the catheter.

The mitral valve prosthesis 1 is then collapsed and fed into the second end of the catheter 18, with the second end 8 of the collapsed valve body 2 leading. An elongate prosthesis guide element 29 is detachably attached to the prosthesis 1, here by way of the screw threaded coupling 25 of the anchor device 5. The prosthesis guide element 29 may be a further guide wire with a cooperating screw threaded coupling 30 on its end, or alternatively might be a narrower catheter. The prosthesis 1 is advanced along the catheter 18 toward the catheter first end 27 as shown in FIG. 12. Rather than using a screw threaded coupling arrangement 25, 30 to couple the anchor device 25 and prosthesis guide element 29, a clip, clamp or the like may be utilized.

Figure 13:
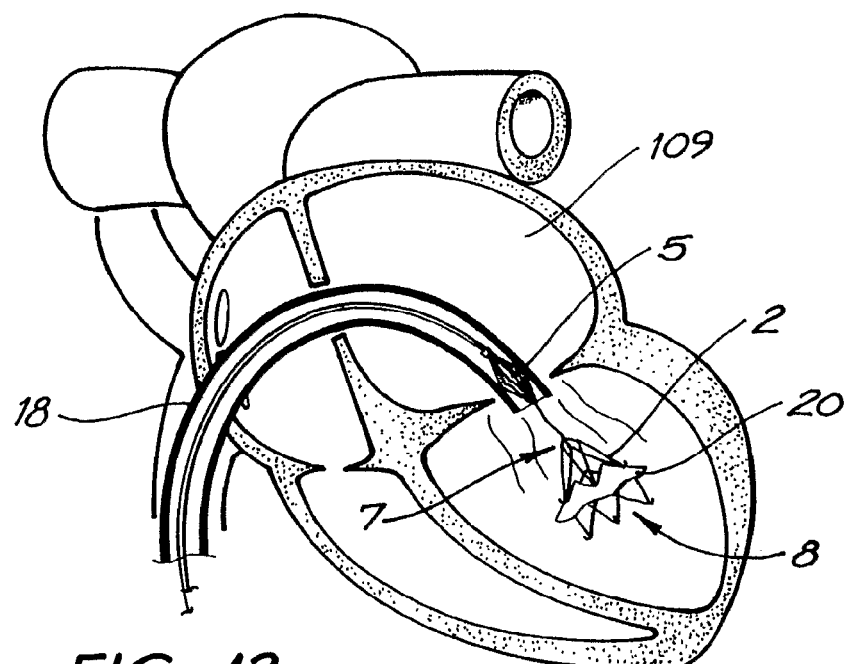
FIG. 13 is a schematic cross-sectional front elevation view of the heart of FIG. 10 with the valve body of the prosthesis released from the catheter into the left ventricle.

The prosthesis 1 is advanced until the valve body 1 is released past the catheter first end 27 and into the left ventricle 110 as shown in FIG. 13. As the valve body 2 is released from the catheter first end 27, the elasticity of the valve body frame results in the valve body 2 extending to its uncollapsed state. The valve body 2 remains attached to the anchor device 5 by way of the anchor line 6.

Figure 14:
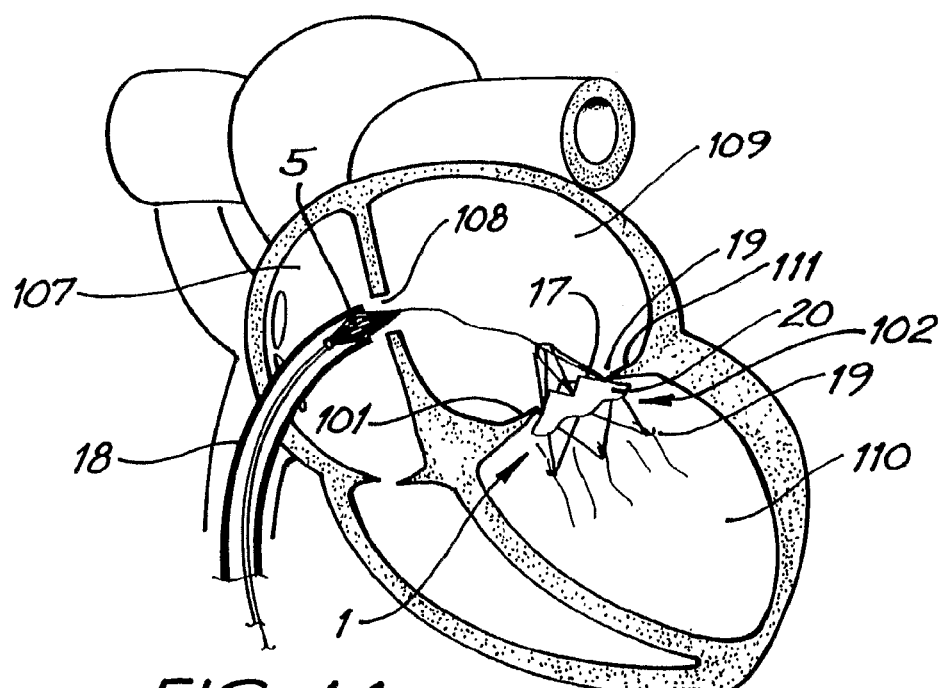
FIG. 14 is a front elevation view of the heart of FIG. 10 with the catheter withdrawn into the right atrium and the prosthesis valve body located in the mitral valve orifice.

Referring to FIG. 14, the catheter 18 is then withdrawn through the puncture 108 such that the catheter first end 27 is located in the right atrium 107. Simultaneously, the prosthesis guide element 29 is withdrawn so as to draw the expanded valve body 2 toward the native mitral valve orifice 102 and left atrium 109. As the valve body first end 7 is sized to enable it to pass through the mitral valve orifice 102, and the valve body 2 is tapered such that the valve body second end 8 is sized so as not to pass through the mitral valve orifice 102, the valve body 2 engages the annular wall 111 of the mitral valve orifice and thus becomes wedged within the valve orifice 102. The valve body diagonal elements 17 and valve leaflets 3, 4 are ideally positioned adjacent the native mitral valve 101, whose leaflets are pushed away and crushed against the mitral valve orifice wall 111 by the valve body 2. Accordingly, with the native mitral valve 101 being pushed away from the mitral valve orifice 102, there is no need to remove the native mitral valve 101.

The barbs 19 protruding from the valve body 2 and facing towards the valve body first end 7 (and thus the left atrium 109) pierce into the valve orifice wall 111 as the valve body 2 is wedged into position. The barbs 19 located adjacent the valve leaflets 3, 4 engage the valve orifice wall 111 in the vicinity of the native valve leaflets, whilst the barbs 19 at the valve body second end 8 engage additional cardiac structure surrounding the lower end of the valve orifice 102 within the left ventricle 110.

The peripheral skirt 20 extending about the valve body 2 is located on the ventricular side of the mitral valve orifice 102, so as to seal between the periphery of the valve body 2 and the mitral valve orifice wall 111 when the left ventricle 110 contracts and pressurises during ventricular systole.

Figure 15:
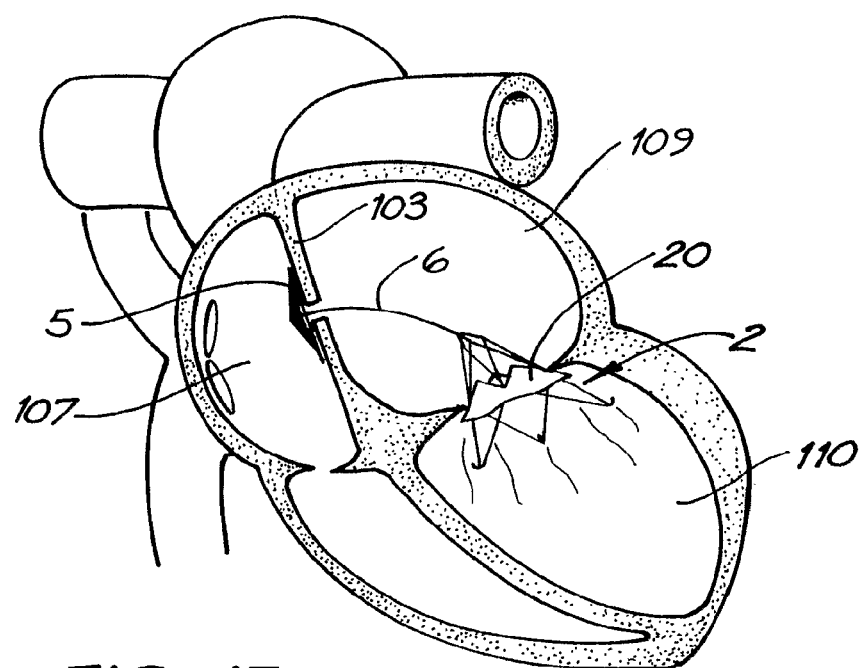
FIG. 15 is a schematic cross-sectional elevation view of the heart of FIG. 10 with the prosthesis fully deployed.
Figure 16:
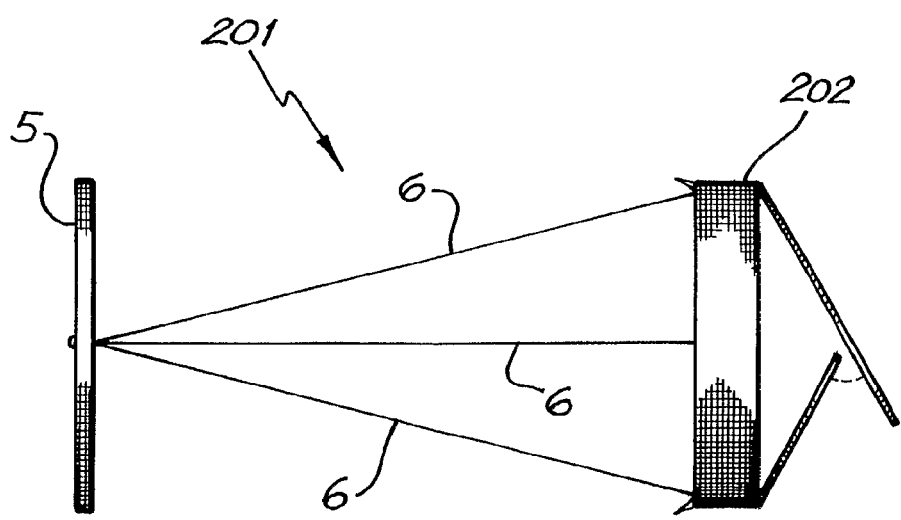
FIG. 16 is a front elevation view of an alternative percutaneous heart valve prosthesis.
Figure 17:
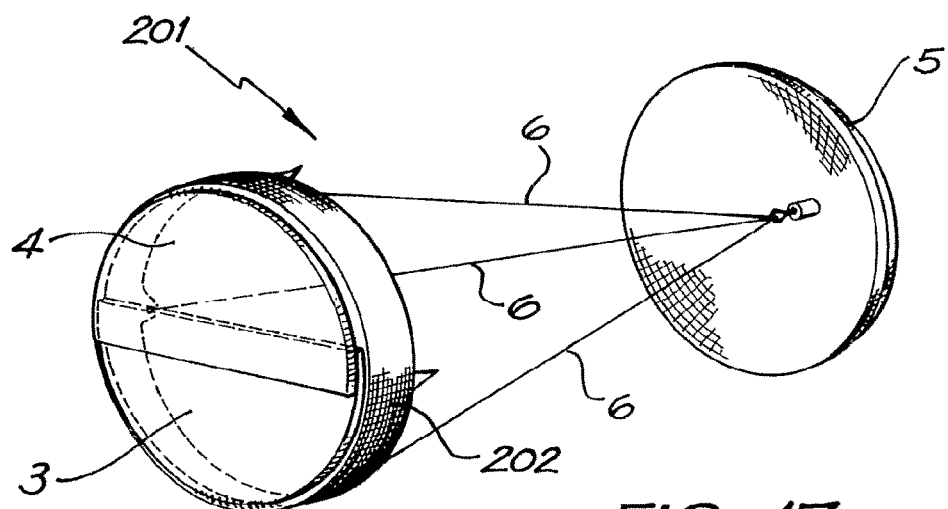
FIG. 17 is a further view of the prosthesis of FIG. 16.

The catheter 18 is then further retracted such that the anchor device 5 is released from the catheter first end 27. As the anchor device 5 is released it expands to its uncollapsed state and, with appropriate sizing of the anchor line 6, engages the inter-atrial septum 103 from within the right atrium 107, as shown in FIG. 15. The catheter 18 and guide wire 26 are then drawn back through the venous system and removed from the patient to complete the procedure. At any stage during the deployment process, the anchor device 5 and valve body 2 may be retracted back into the catheter 18 and removed if any difficulties are encountered.

The anchor device 5 thus securely anchors the valve body 2 in the mitral valve orifice 102 against migration towards the left ventricle 110 during atrial systole, when the left atrium 109 contracts and pressurizes. The tapered configuration of the valve body 2, effectively wedging the valve body 2 into the mitral valve orifice 102, anchors the valve body 2 against migration towards the left atrium 109 during ventricular systole. The barbs 19 additionally anchor the valve body 2 against migration towards the left atrium 109.

Once the prosthesis is successfully in place, the prosthesis guide element 29 is detached from the anchor device 5, by rotating the prosthesis guide element 29 to thereby decouple the threaded coupling.

The entire procedure may be performed under the guidance of fluoroscopy, transthoracic and transesophageal echocardiography in a known manner.

The valve leaflets 3, 4 replace the function of the native mitral valve leaflets, allowing bloodflow from the left atrium 109 to the left ventricle 110 through the mitral valve orifice 102 and bloodflow passage 9 of the valve body 2 during atrial systole, whilst blocking retrograde flow from the left ventricle 110 to the left atrium 109 during ventricular systole. The peripheral skirt 20 further blocks bloodflow through any gaps between the valve body 2 and the mitral valve orifice wall 111 in the retrograde direction during ventricular systole.

In addition to, or in place of, the barbs 19 and tapered shape of the valve body 2 anchoring the valve body 2 against migration towards the left atrium 109, a further anchor device 5 might be utilized to anchor the valve body 2 to the inter-ventricular septum 112. Similarly, the tapered form of the valve body 2 might be utilized in conjunction with other mechanisms for securing the valve body 2 against migration towards the left ventricle rather than utilizing the anchor device. It is further envisaged that the general valve prosthesis configuration may be utilized for other types of heart valve prosthesis, for replacement of the aortic semiluminar valve, pulmonary semiluminar valve or tricuspid valve, utilizing alternative structures of the heart for securing the anchor device.

An alternate form of valve prosthesis 201 is depicted in FIGS. 16 to 20. The prosthesis 201 has an anchor device 5 much the same as that of the prosthesis 1 of FIG. 1, however the valve body 202 is in the general form of a collapsible cylindrical ring. The collapsible ring 202 is formed of a squat cylinder and may have a woven construction formed of elongate elastic elements, typically metallic wire. Again, a particularly suitable material is a superelastic shape memory material such as nitinol. The valve body ring 202 should be sized so as to have an undeformed diameter slightly larger than that of the mitral valve orifice 102, such that when deployed, a compressive force is applied to the wall 111 of the valve orifice 102 to assist retaining the valve body in place. Care should be taken, however, not to oversize the valve body ring 202 such that an excessive compressive force is applied to the mitral valve orifice wall 111 which, as discussed above, may result in collapsing of the aortic outflow tract.

Figure 18:
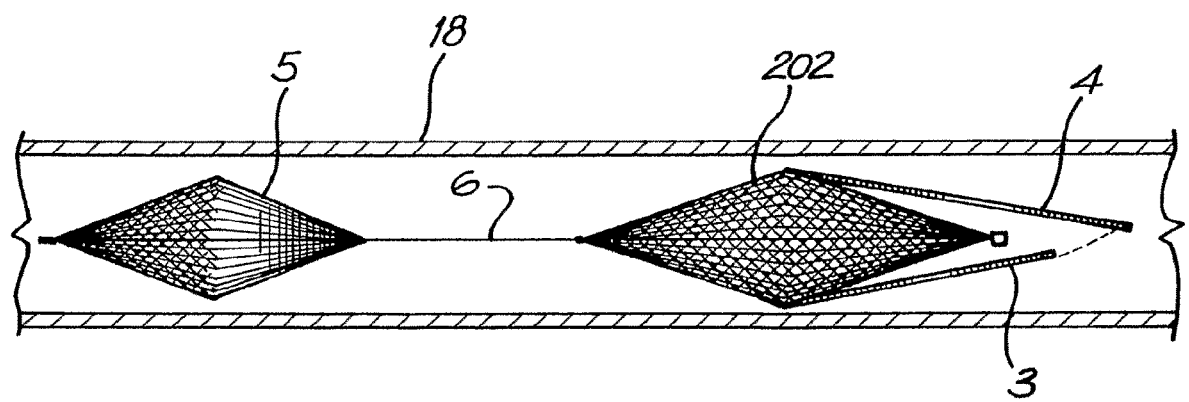
FIG. 18 is a front elevation view of the prosthesis of FIG. 16 in a collapsed state located in a catheter.

The valve body ring 202 is arranged such that it may be collapsed into a cylindrical shape of reduced diameter, enabling it to be loaded into a catheter 18, as depicted in FIG. 18 in a similar manner to the valve body 2 described above.

Valve leaflets 3, 4, as described above in relation to the first prosthesis 1, are secured to the valve body ring 202, again typically by suturing. Here three anchor lines 6 secure the valve body ring 202 to the anchoring device 5, with the anchor line 6 being secured at points spaced equidistantly about the valve body ring 202.

Prongs 19 protrude from the valve body ring 202 toward the anchoring device 5 for engaging the valve orifice wall 111 in much the same manner as discussed above.

Figure 19:
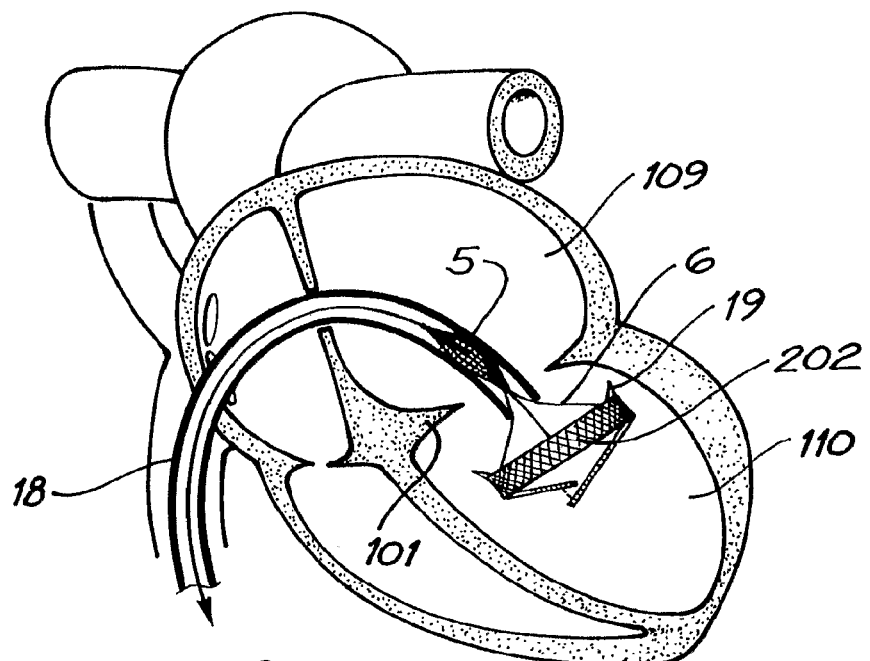
FIG. 19 is a schematic cross-sectional front elevation view of a heart with a partially deployed prosthesis of FIG. 16.
Figure 20:
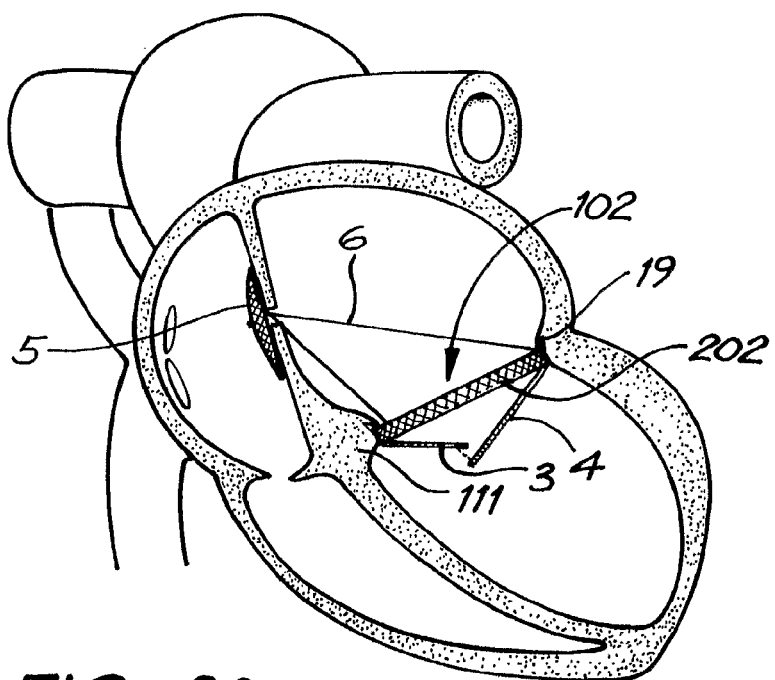
FIG. 20 is a schematic cross-sectional front elevation view of the heart of FIG. 19 with the prosthesis fully deployed.

Referring to FIGS. 19 and 20, deployment of the prosthesis 201 is generally the same as that described above in relation to the first prosthesis 1, with the primary difference being the lack of a tapered body that is wedged into the mitral valve orifice 102 to assist anchoring against migration towards the left atrium 109. The valve body ring 202 thus relies on the barbs 19 and compressive force applied to the mitral valve orifice wall 111 to prevent migration towards the left atrium 109.

What is claimed is:

1. A method of implanting a valve prosthesis in a native heart valve, comprising:
    advancing a catheter through a patient's venous system, wherein a valve prosthesis is held in a collapsed state along a distal end portion of the catheter, the valve prosthesis comprising:
        a valve body frame having a first end, a second end, a longitudinal axis, and a blood flow passage extending along the longitudinal axis between the first end and the second end, the valve body frame being collapsible about the longitudinal axis to fit within the catheter for delivery, the valve body frame formed by a plurality of sub-frame members, each sub-frame member having a general form of a rhombus with acute-angled vertices and oblique-angled vertices;
        a flexible skirt made from polyester, the flexible skirt extending around a periphery of the valve body frame, the flexible skirt dimensioned for blocking blood flow between the valve body frame and native heart valve tissue;
        a one-way valve positioned within the valve body frame, the one-way valve including a plurality of flexible valve leaflets for permitting blood to flow from the first end of the valve body frame to the second end of the valve body frame, the flexible valve leaflets comprising pericardial material; and
        a plurality of barbs spaced about the periphery of the valve body frame, wherein at least some barbs are positioned at the oblique-angled vertices and wherein at least some barbs are positioned at the acute-angled vertices along the second end of the valve body frame, wherein each of the barbs points toward the first end of the valve body frame for engaging native heart valve tissue;
    releasing the valve prosthesis from the catheter and allowing the valve prosthesis to radially expand in the native heart valve; and
    withdrawing the catheter from the patient's venous system;
    wherein the barbs secure the valve prosthesis within the native heart valve and wherein the one-way valve replaces the function of the native heart valve;
    wherein adjacent sub-frame members are joined at the oblique-angled vertices.

2. The method of claim 1, wherein the native heart valve is a mitral valve.

3. The method of claim 2, wherein the distal end portion of the catheter is advanced through a femoral vein and toward the right atrium.

4. The method of claim 3, wherein the distal end portion of the catheter is further advanced through a puncture formed in the inter-atrial septum.

5. The method of claim 4, wherein the distal end portion of the catheter is further advanced through the left atrium and at least partially into a left ventricle.

6. The method of claim 1, wherein the valve body frame is made of a nickel-titanium alloy.

7. The method of claim 1, wherein each sub-frame member is formed of elongate valve body frame elements.

8. The method of claim 7, wherein the elongate valve body frame elements have thicknesses of about 0.3 to 0.4 mm.

* * * * *